United States Patent [19]

Tomisawa et al.

[11] Patent Number: 4,594,197
[45] Date of Patent: Jun. 10, 1986

[54] 3-BENZOYL-2-MERCAPTOPROPIONIC ACID DERIVATIVES

[75] Inventors: Kazuyuki Tomisawa, Saitama; Kazuya Kameo; Toru Matsunaga, both of Ageo; Shiuji Saito, Niiza; Yoshimoto Nakashima, Ageo; Kaoru Sota, Tokorozawa, all of Japan

[73] Assignee: Taisho Pharmaceutical Co., Ltd., Tokyo, Japan

[21] Appl. No.: 646,230

[22] Filed: Aug. 31, 1984

[30] Foreign Application Priority Data

Sep. 3, 1983 [JP] Japan ................... 58-162446

[51] Int. Cl.$^4$ .................. C07C 149/40; C07C 157/09; C07C 153/023
[52] U.S. Cl. ...................... 558/255; 560/15; 562/426
[58] Field of Search ............ 260/455 R; 560/15; 562/426

[56]  References Cited

U.S. PATENT DOCUMENTS 4,472,316  9/1984  Sota et al. .................. 260/455 R

FOREIGN PATENT DOCUMENTS 0088585  9/1983  European Pat. Off. ........ 260/455 R
1468344  8/1973  Fed. Rep. of Germany ... 260/455 R
2746754  4/1978  Fed. Rep. of Germany ... 260/455 R Primary Examiner—Henry R. Jiles
Assistant Examiner—Robert C. Whittenbaugh
Attorney, Agent, or Firm—Cushman, Darby & Cushman

[57] ABSTRACT

3-Benzoyl-2-mercaptopropionic acid derivatives represented by the general formula

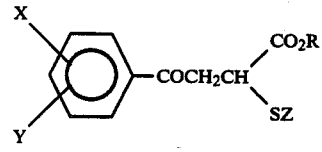

(wherein, X represents a hydrogen atom, a halogen atom, hydroxy group, a lower alkyl group or a lower alkoxy group, Y represents a hydrogen atom, a halogen atom, a lower alkyl group or a lower alkoxy group, Z represents a hydrogen atom or an acyl group, and R represents a hydrogen atom or a lower alkyl group). These compounds have immunomodulative function and are effective for the treatment of diseases caused by abnormal immunofunction.

9 Claims, No Drawings

3-BENZOYL-2-MERCAPTOPROPIONIC ACID DERIVATIVES

BACKGROUND OF THE INVENTION

The present invention relates to novel 3-benzoyl-2-mercaptopropionic acid derivatives, and more particularly, it relates to 3-benzoyl-2-mercaptopropionic acid derivatives which have immunomodulative function and are effective for treatment of diseases caused by abnormal immunofunction.

In the past, there have been used the so-called immunosuppressors for treatment of autoimmune diseases such as chronic rheumatoid arthritis. In general, however, the suppressive activity of the agents is mainly based on cytotoxicity. Accordingly, because of a strong side-effect depending on the above-mentioned cytotoxicity, these agents can not be said to be appropriate as therapeutical agents of autoimmune diseases which are required to be administered continuously for a long term.

Further, in order to treat diseases related to immune, there have been recently used the so-called immunomodulators which have the effect to regulate the immune function, i.e., either stimulate the immune function when lowered, or suppress the immune function when augmented. However, even these agents cannot be said to be satisfactory in aspects of effect, side-effect and toxicity.

As a result of the ernest studies, the present inventors have found that certain 3-benzoyl-2-mercaptopropionic acid derivatives have good immunomodulative function, weak side-effect and weak toxicity, and thus the present invention has been completed.

SUMMARY OF THE INVENTION

An object of the present invention is to provide novel 3-benzoyl-2-mercaptopropionic acid derivatives which have immunomodulative function and are effective for treatment of diseases caused by abnormal immunofunction and the process for producing them.

Other objects and advantages of the present invention will be apparent from the following descriptions.

DETAILED DESCRIPTIONS OF THE INVENTION

The present invention is illustrated in detail hereunder.

The objective compounds of the present invention are 3-benzoyl-2-mercaptopropionic acid derivatives (hereinafter referred to as Compound I) having the general formula:

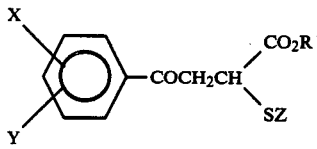

(wherein, X represents a hydrogen atom, a halogen atom, a hydroxy group, a lower alkyl group or a lower alkoxy group, Y represents a hydrogen atom, a halogen atom, a lower alkyl group or a lower alkoxy group, Z represents a hydrogen atom or an acyl group, and R represents a hydrogen atom or a lower alkyl group).

Here, the halogen atom for X and Y is a fluorine, chlorine or bromine atom, and the lower alkyl group for X and Y are a methyl group, an ethyl group, a propyl group, an isopropyl group and the like, and the lower alkoxy group for X and Y are a methoxy group, an ethoxy group and the like.

The acyl group for Z are an aliphatic acyl group such as an acetyl group, a propionyl group, a butyryl group and the like, or an aromatic acyl group such as a benzoyl group, a toluoyl group and the like.

The lower alkyl group for R are a methyl group, an ethyl group, a propyl group, an isopropyl group and the like.

The compound I can be prepared, for example, by the following method.

(1) A compound represented by the general formula

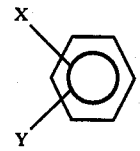

(wherein, X and Y are as defined above) is reacted with maleic anhydride according to Friedel-Crafts reaction to give a carboxylic acid (hereinafter referred to as Compound II) represented by the general formula

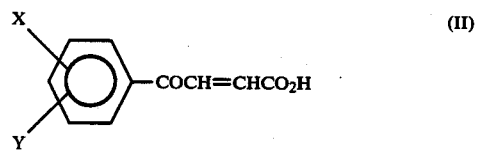

(wherein, X and Y are as defined above), or (2) a methylketone compound represented by the general formula

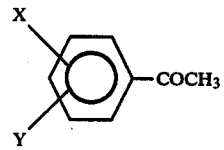

(wherein, X and Y are as defined above) is reacted with glyoxylic acid hydrate in the absence of solvent under reduced pressure of 1 to 100 mmHg at 80° to 120° C. for 2 to 10 hours for condensation to give a compound represented by the general formula

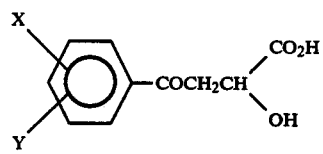

(wherein, X and Y are as defined above), which is then heated, or refluxed under heating in an organic solvent (e.g., benzene, toluene, xylene, dioxane, acetic acid and the like) in the presence of an acid catalyst (e.g., sulfuric acid, hydrochloric acid, p-toluenesulfonic acid, potassium bisulfate and the like) at 80° to 120° C. for dehydration for 1 to 10 hours to give the compound II.

(3) The compound II is reacted with a conventional alkylating agent having R' which represents the lower alkyl group for the above R (e.g., an alkyl halide, a dialkyl sulfate and the like) in an organic solvent (e.g., acetone, dimethylformamide, hexamethylphosphoric triamide, dimethylsulfoxide and the like) in the presence of a base (e.g., sodium carbonate, potassium carbonate, lithium carbonate, sodium hydrogencarbonate, potassium hydrogencarbonate, sodium hydride, potassium hydride, sodium hydroxide, potassium hydroxide, sodium alkoxide and the like) to give an alkyl ester compound (hereinafter referred to as Compound III) represented by the general formula

(wherein, X, Y and R' are as defined above).

(4) The compound II or III is dissolved in an organic solvent (e.g., methanol, ethanol, t-butanol, hexane, benzene, toluene, diethyl ether, dimethoxyethane, dioxane, dichloromethane, chloroform, carbon tetrachloride, carbon disulfide, acetone, ethyl acetate, dimethylformamide, hexamethylphosphoric triamide, dimethyl sulfoxide, and the like), and a thiocarboxylic acid having the acyl group for the above Z is added in amount of equimolar to two times the compound II or III. The mixture is reacted at $-20°$ to $50°$ C. for 0.5 to 24 hours to give the compound of the formula I wherein Z is an acyl group.

(5) A thioester compound of the formula I wherein Z is an acyl group is subjected to acidic hydrolysis or reacted with hydrazine in an organic solvent (e.g., methanol, ethanol, t-butanol, diethyl ether, dimethoxyethane, tetrahydrofuran, dioxane and the like) at $-20°$ to $50°$ C. to give the compound of the formula I wherein Z is a hydrogen atom.

This compound is reacted with an acid halide or acid anhydride having the acyl group for the above Z in the presence of a base for acylation to convert into the compound of the formula I wherein Z is an acyl group.

The compound I has a good immunomodulative function, low side-effect and low toxicity, therefore they are useful therapeutical agents of the diseases caused by abnormal immunofunction, for example, rheumatoid arthritis, autoimmune diseases, cancer, bacterial infectious diseases, asthma and the like. For the purposes, the compound of the present invention may be administered orally or parenterally in a conventional dosage form such as tablets, capsules, powders, granules, syrups, and injectional forms prepared according to conventional pharmaceutical practices.

The effective dosage of the compound of the present invention depends on the age, weight or response of the patient. Generally, however, the daily dosage in adults may range from 0.1 to 3 g, preferably 0.3 to 1.5 g in single or divided doses.

The preferred compounds of the present invention are the compounds of formula I wherein X is a hydrogen atom, a halogen atom or a methyl group, Z is a hydrogen atom or an acetyl group and each of Y and R is a hydrogen atom.

The present invention is concretely illustrated below by Experiments and Examples, but the invention is not limited thereto.

EXPERIMENT 1

Effect to adjuvant arthritis (chronic rheumatoid arthritis model)

10 Female Sprague-Dawley rats, 8 weeks old, weighing 160–190 g were used per each group. Rats of each group were administered subcutaneously into the tail with a suspension of 0.6 mg of heated killed mycobacterium butyricum in liquid parafin. Each of the compounds I, suspended in a 5% gum arabic solution, was administered orally once a day to rats of each group after the sensitization. The symptoms of arthritis were evaluated by the severities of the inflammation of arthritis at each of 6 sites on limbs and ears as 5 stages which are scored as 0, 1, 2, 3 and 4, and expressed as the summing-up score (24 points) at a given interval, i.e., inflammation score.

Table 1 shows the scores of the controls (drug-untreated group) and the drug-treated group 21 days after sinsitization.

TABLE 1

| Compound number | Dose (mg/kg) | Inflammation score | Inflammation suppression rate to control group |
|---|---|---|---|
| 1 | 10 | 6.1 ± 1.4 | 3 |
|  | 100 | 4.0 ± 1.3 | 37 |
|  | 300 | 1.7 ± 0.4 | 73 |
| 11 | 100 | 4.4 ± 0.9 | 30 |
| 12 | 100 | 1.5 ± 0.5 | 76 |
| 25 | 100 | 5.5 ± 1.2 | 13 |
| Control group | — | 6.3 ± 1.7 | — |

Note
Compound number means a compound which is prepared in the following Example attached the same number of Example as that of the compound in Table 1.

It is recognized from the above results that the compounds I suppress strongly the adjuvant arthritis and possess immunomodulative and anti-arthritic activities.

EXPERIMENT 2

Effect to humoral antibody formation under hypotensive state (Recovery effect of immunodeficiency)

6–8 Female $BDF_1$ mice, 8–12 weeks old, weighing 18–22 g were used per each group. Mice of each group were administered intravenously with $4 \times 10^6$ sheep red blood cells as antigen to be sensitized.

Each of the compounds I, suspended in 5% gum arabic saline solution, was administered intraperitoneally to mice of each group 2 hours after the sensitization.

Number of antibody-forming cells in the spleen cells of mice was determined 4 days after the sensitization according to the method of Cunningham and Szenberg (Immunology, vol. 14, page 599, 1968).

The results are shown in Table 2.

TABLE 2

| Compound number | Dose (mg/kg) | Number of antibody-forming cells/spleen | Enhancement rate of antibody formation |
|---|---|---|---|
| 1 | 0 | 8088 ± 1842 | 1.00 |
|  | 1 | 14400 ± 2021* | 1.78 |
|  | 10 | 14663 ± 2020* | 1.81 |
|  | 100 | 16371 ± 6085* | 2.02 |
| 4 | 0 | 6714 ± 1553 | 1.00 |
|  | 1 | 6450 ± 1008 | 0.96 |
|  | 10 | 12429 ± 1840* | 1.85 |

TABLE 2-continued

| Compound number | Dose (mg/kg) | Number of antibody-forming cells/spleen | Enhancement rate of antibody formation |
|---|---|---|---|
| | 100 | 8960 ± 1250 | 1.34 |

Note
(1) Compound number means a compound which is prepared in the following Example attached the same number of Example as that of the compound in the Table.
(2) *significant at p < 0.05 by T-test.

It is recognized from the above results that the compounds I increase the number of antibody-forming cells and have the recovery effect of immunodeficiency.

EXPERIMENT 3

Effect to delayed-type footpad reaction (Cellular immunostimulation)

6-8 Female $BDF_1$ mice, 8-12 weeks old, weighing 18-22 g were used per each group. Mice of each group were administered subcutaneously into the right footpad with $1 \times 10^8$ sheep red blood cells as antigen to be sensitized.

Each of the compounds I, suspended in a 5% gum arabic saline solution, was administered intraperitoneally to mice of each group 2 hours after the sensitization.

Four days after the sensitization, mice of each group were administered subcutaneously into the left footpad with $1 \times 10^8$ sheep red blood cells, and the increase of thickness of swelling footpad was determined according to the method of Lagrange et al (Journal of Experimental Medicine, vol. 193, page 528, 1974).

The results are shown in Table 3.

TABLE 3

| Compound number | Dose (mg/kg) | Increase of thickness of swelling footpad ($\times 10^{-2}$ mm) | Enhancement rate of delayed-type footpad reaction |
|---|---|---|---|
| 1 | 0 | 153.8 ± 10.9 | 1.00 |
| | 10 | 176.3 ± 5.4 | 1.15 |
| | 100 | 188.6 ± 11.1* | 1.23 |
| 4 | 0 | 118.9 ± 8.4 | 1.00 |
| | 10 | 121.3 ± 8.2 | 1.02 |
| | 100 | 150.6 ± 6.2** | 1.27 |

Note
(1) Compound number means a compound which is prepared in the following Example attached the same number of Example as that of the compound in Table.
(2) *significant at p < 0.05 by T-test.
**significant at p < 0.01 by T-test.

It is recognized from the above results that the compounds I stimulate the delayed-type footpad reaction and have the cellular immunopotentiating effect.

EXPERIMENT 4

Acute toxicity test

Male, 8 weeks old ICR mice (body weight of 28-32 g, 8 mice per each group) were administered orally with a suspension of the compound of Example 1 in 5% gum arabic solution, and observed for 7 days, and the $LD_{50}$ value was calculated.

The $LD_{50}$ value of the compound of Example 1 was excess of 1000 mg/kg.

EXAMPLE 1

To a solution of 1.76 g of 3-benzoylacrylic acid in 30 ml of diethyl ether was added 0.8 ml of thioacetic acid, and the resulting mixture was stirred at room temperature for 5 hours. The diethyl ether was removed from the reaction mixture by evaporation under reduced pressure, and the residue was purified by silica gel column chromatography using a mixture of hexane and dichloromethane as an eluent and recrystallized from a mixture of hexane and diethyl ether to give 2.09 g of 2-acetylthio-3-benzoylpropionic acid.

m.p. 90°–ρ° C.

Elementary Anal. for $C_{12}H_{12}O_4S$. Calcd. (%) : C 57.13, H 4.80. Found (%): C 57.18, H 4.84

EXAMPLE 2

(1) A mixture of 6.70 g of o-methylacetophenone and 4.60 g of glyoxylic acid hydrate was heated at 95° C. under reduced pressure of 25 mmHg for 3 hours. The reaction mixture was dissolved in a 5% aqueous solution of potassium carbonate. The resulting solution was washed with ethyl acetate, made slightly acidic with dil. hydrochloric acid, and extracted with ethyl acetate. The organic layer was washed with water and dried over magnesium sulfate. The solvent was removed by evaporation under reduced pressure to give a viscous oil.

To the oil were added 10 ml of glacial acetic acid and 1 ml of conc. hydrochloric acid. The mixture was refluxed by heating with stirring for 3 hours. The acetic acid was removed from the mixture by evaporation under reduced pressure, and the residue was dissolved in ethyl acetate. The solution was washed with water and dried over magnesium sulfate. The ethyl acetate was removed from the solution by evaporation, and the residue was recrystallized from a mixture of hexane and diethyl ether to give 4.85 g of 3-(2-methylbenzoyl)acrylic acid.

m.p. 82°–83° C.

(2) Following the procedure of Example 1 using 1.9 g of 3-(2-methylbenzoyl) acrylic acid in place of 3-benzoylacrylic acid, there was obtained 2.50 g of 2-acetylthio-3-(2-methylbenzoyl)propionic acid.

m.p. 106°–108° C.

Elementary Anal. for $C_{13}H_{14}O_4S$. Calcd. (%): C 58.63, H 5.30. Found (%): C 58.63, H 5.34.

EXAMPLE 3

(1) Following the procedure of Example 2-(1) using 6.70 g of m-methylacetophenone in place of o-methylacetophenone, there was obtained 5.61 g of 3-(3-methylbenzoyl)acrylic acid.

m.p. 115°–117° C.

(2) Following the procedure of Example 1 using 1.90 g of 3-(3-methylbenzoyl)acrylic acid in place of 3-benzoylacrylic acid, there was obtained 2.42 g of 2-acetylthio-3-(3-methylbenzoyl)propionic acid.

m.p. 74°–76° C.

Elementary Anal. for $C_{13}H_{14}O_4S$. Calcd. (%): C 58.63, H 5.30. Found (%): C 58.61, H 5.37.

EXAMPLE 4

Following the procedure of Example 1 using 1.90 g of 3-(4-methylbenzoyl)acrylic acid in place of 3-benzoylacrylic acid, there was obtained 1.60 g of 2-acetylthio-3-(4-methylbenzoyl)propionic acid.

m.p. 81°–85° C.

Elementary Anal. for $C_{13}H_{14}O_4S$. Calcd. (%): C 58.63, H 5.30. Found (%): C 58.88, H 5.33

EXAMPLE 5

Following the procedure of Example 1 using 2.18 g of 3-(4-isopropylbenzoyl)acrylic acid in place of 3-benzoylacrylic acid, there was obtained 2.29 g of 2-acetylthio-3-(4-isopropylbenzoyl)propionic acid.

m.p. 84°–86° C.

Elementary Anal. for $C_{15}H_{18}O_4S$. Calcd. (%): C 61.20, H 6.16. Found (%): C 61.09, H 6.16.

EXAMPLE 6

Following the procedure of Example 1 using 1.92 g of 3-(4-hydroxybenzoyl)acrylic acid in place of 3-benzoylacrylic acid, there was obtained 2.11 g of 2-acetylthio-3-(4hydroxybenzoyl)propionic acid.

m.p. 147°–148° C. (decomposition)

Elementary Anal. for $C_{12}H_{12}O_5S$. Calcd. (%): C 53.72, H 4.51. Found (%): C 53.46, H 4.51.

EXAMPLE 7

Following the procedure of Example 1 using 2.06 g of 3-(3-methoxybenzoyl)acrylic acid in place of 3-benzoylacrylic acid, there was obtained 2.62 g of 2-acetylthio-3-(3-methoxybenzoyl)propionic acid as an oil.

$IR\nu_{max}^{neat}$, cm$^{-1}$: 1740–1680 (carbonyl).

NMR(CDCl$_3$), ppm: 2.38 (3H, s), 3.58 (1H, dd, J=18 Hz, 5 Hz), 3.69 (1H, dd, J=18 Hz, 8 Hz), 3.85 (3H, s), 4.76 (1H, dd, J=8 Hz, 5 Hz), 7.14 (1H, bd, J=8 Hz), 7.38 (1H, t, J=8 Hz), 7.50 (2H, m).

EXAMPLE 8

(1) In 200 ml of dichloromethane were dissolved 5.4 g of anisol and 4.98 g of maleic anhydride, and 9.95 g of anhydrous aluminum chloride was added gradually under ice-cooling with stirring. Then, the mixture was stirred at room temperature for 5 hours. The reaction solution was concentrated under reduced presource, and poured into a mixture of 10 ml of conc. hydrochloric acid and 150 g of ice, and the mixture was extracted with ethyl acetate. The organic layer was washed with water and dried over magnesium sulfate. The ethyl acetate was removed from the solution by evaporation under reduced pressure, and the residue was recrystallized from a mixture of hexane and diethyl ether to give 3.85 g of 3-(4-methoxybenzoyl)acrylic acid.

m.p. 108°–110° C.

(2) Following the procedure of Example 1 using 2.06 g of 3-(4-methoxybenzoyl)acrylic acid in place of 3-benzoylacrylic acid, there was obtained 2.12 g of 2-acetylthio-3-(4-methoxybenzoyl) propionic acid.

m.p. 122°–123.5° C.

Elementary Anal. for $C_{13}H_{14}O_5S$. Calcd. (%): C 55.31, H 5.00. Found (%): C 55.54, H 5.08.

EXAMPLE 9

Following the procedure of Example 1 using 2.11 g of 3-(2-chlorobenzoyl)acrylic acid in place of 3-benzoylacrylic acid, there was obtained 2.46 g of 2-acetylthio-3-(2-chlorobenzoyl)propionic acid.

m.p. 115°–116° C.

Elementary Anal. for $C_{12}H_{11}ClO_4S$. Calcd. (%): C 50.28, H 3.84. Found (%): C 50.21, H 3.96.

EXAMPLE 10

(1) Following the procedure of Example 2-(1) using 7.73 g of m-chloroacetophenone in place of o-methylacetophenone, there was obtained 5.17 g of 3-(3-chlorobenzoyl)acrylic acid.

m.p. 150°–152° C.

(2) Following the procedure of Example 1 using 2.11 g of 3-(3-chlorobenzoyl)acrylic acid in place of 3-benzoylacrylic acid, there was obtained 2.69 g of 2-acetylthio-3-(3-chlorobenzoyl)propionic acid.

m.p. 85°–86° C.

Elementary Anal. for $C_{12}H_{11}ClO_4S$. Calcd. (%): C 50.28, H 3.84. Found (%): C 50.04, H 3.96.

EXAMPLE 11

Following the procedure of Example 1 using 2.11 g of 3-(4-chlorobenzoyl)acrylic acid in place of 3-benzoylacrylic acid, there was obtained 2.64 g of 2-acetylthio-3-(4-chlorobenzoyl)propionic acid.

m.p. 68°–69° C.

Elementary Anal. for $C_{12}H_{11}ClO_4S$. Calcd. (%): C 50.28, H 3.84. Found (%): C 50.40, H 3.91.

EXAMPLE 12

Following the procedure of Example 1 using 2.55 g of 3-(4-bromobenzoyl)acrylic acid in place of 3-benzoylacrylic acid, there was obtained 2.55 g of 2-acethylthio-3-(4-bromobenzoyl)propionic acid.

m.p. 98°–99° C.

Elementary Anal. for $C_{12}H_{11}BrO_4S$. Calcd. (%): C 43.52, H 3.35. Found (%): C 43.70, H 3.37.

EXAMPLE 13

(1) Following the procedure of Example 8-(1) using 4.80 g of fluorobenzene in place of anisol, there was obtained 4.18 g of 3-(4-fluorobenzoyl)acrylic acid.

m.p. 130°–131.5° C.

(2) Following the procedure of Example 1 using 1.94 g of 3-(4-fluorobenzoyl)acrylic acid in place of 3-benzoylacrylic acid, there was obtained 2.19 g of 2-acetylthio-3-(4-fluorobenzoyl)propionic acid.

m.p. 108°–110° C.

Elementary Anal. for $C_{12}H_{11}FO_4S$. Calcd. (%): C 53.33, H 4.10. Found (%): C 53.10, H 4.17.

EXAMPLE 14

Following the procedure of Example 1 using 2.04 g of 3-(2,4-dimethylbenzoyl)acrylic acid in place of 3-benzoylacrylic acid, there was obtained 2.32 g of 2-acetylthio-3-(2,4-dimethylbenzoyl)propionic acid.

m.p. 101°–102° C.

Elementary Anal. for $C_{14}H_{16}O_4S$. Calcd. (%): C 59.98, H 5.75. Found (%): C 59.85, H 5.80.

EXAMPLE 15

Following the procedure of Example 1 using 2.04 g of 3-(3,4-dimethylbenzoyl)acrylic acid in place of 3-benzoylacrylic acid, there was obtained 2.35 g of 2-acetylthio-3-(3,4-dimethylbenzoyl)propionic acid as an oil.

$IR\nu_{max}^{CHCl_3}$, cm$^{-1}$: 1710 14 1680 (carbonyl).

NMR(CDCl$_3$), ppm: 2.30 (6H, s), 2.36 (3H, s), 3.54 (1H, dd, J=16 Hz, 7 Hz), 3.66 (1H, dd, J=16 Hz, 6 Hz), 4.74 (1H, dd, J=7 Hz, 6 Hz), 7.21 (1H, d, J=8 Hz), 7.66 (1H, d, J=8 Hz), 7.72 (1H, d, J=8 Hz), 10.10 (1H, bs).

EXAMPLE 16

(1) Following the procedure of Example 8-(1) using 6.90 g of 1,2-dimethoxybenzene in place of anisol, there was obtained 4.37 g of 3-(3,4-dimethoxybenzoyl)acrylic acid.

m.p. 174°–175° C.

(2) Following the procedure of Example 1 using 2.36 g of 3-(3,4-dimethoxybenzoyl)acrylic acid in place of 3-benzoylacrylic acid, there was obtained 2.53 g of 2-acetylthio-3-(3,4-dimethoxybenzoyl)propionic acid.
m.p. 110°-112° C.

Elementary Anal. for $C_{14}H_{16}O_6S$. Calcd. (%): C 53.84, H 5.16. Found (%): C 53.69, H 5.09.

EXAMPLE 17

Following the procedure of Example 1 using 2.45 g of 3-(2,4-dichlorobenzoyl)acrylic acid in place of 3-benzoylacrylic acid, there was obtained 2.70 g of 2-acetylthio-3-(2,4-dichlorobenzoyl)propionic acid.
m.p. 73°-74.5° C.

Elementary Anal. for $C_{12}H_{10}Cl_2O_4S$. Calcd. (%): C 44.88, H 3.14. Found (%): C 44.74, H 3.14.

EXAMPLE 18

Following the procedure of Example 1 using 2.45 g of 3-(3,4-dichlorobenzoyl)acrylic acid in place of 3-benzoylacrylic acid, there was obtained 2.63 g of 2-acetylthio-3-(3,4-dichlorobenzoyl)propionic acid.
m.p. 102.5°-105° C.

Elementary Anal. for $C_{12}H_{10}ClO_2O_4S$.
Cacld. (%): C 44.88, H 3.14. Found (%): C 45.05, H 3.19.

EXAMPLE 19

1.90 g of methyl 3-benzoylacrylate was dissolved in 30 ml of diethyl ether, and 0.8 ml of thioacetic acid was added thereto. The mixture was stirred for 5 hours at room temperature. The reaction solution was washed, in turn, with water, a saturated aqueous solution of sodium hydrogencarbonate and water, and dried over magnesium sulfate. The diethyl ether was removed from the solution by evaporation, and the residue was purified by silica gel column chromatography using a mixture of hexane and diethyl ether as an eluent, and then recrystallized from the same mixture to give 2.42 g of methyl 2-acetylthio-3-benzoylpropionate.
m.p. 53.5°-54° C.

Elementary Anal. for $C_{13}H_{14}O_4S$. Calcd. (%): C 58.63, H5.30. Found (%): C 58.88, H 5.30.

EXAMPLE 20

Following the procedure of Example 19 using 2.04 g of ethyl 3-benzoylacrylate in place of methyl 3-benzoylacrylate, there was obtained 2.60 g of ethyl 2-acetylthio-3-benzoylpropionate as an oil.

$IR\nu_{max}^{neat}$, cm$^{-1}$: 1740 (ester, thioester), 1690 (ketone).

NMR(CDCl$_3$), ppm: 1.27 (3H, t, J=7 Hz), 2.38 (3H, s), 3.58 (1H, dd, J=16 Hz, 5 Hz), 3.74 (1H, dd, J=16 Hz, 7 Hz), 4.23 (2H, q, J=7 Hz), 4.73 (1H, dd, J=7 Hz, 5 Hz), 7.44-7.64 (3H, m), 7.98 (2H, d, J=8 Hz).

EXAMPLE 21

(1) To a solution of 3.52 g of 3-benzoylacrylic acid in 30 ml of dimethylformamide were added 8 ml of isopropylbromide, 5.5 g of potassium carbonate and a catalystic amount of sodium iodide. The mixture was stirred at room temperature for 4 hours and allowed to stand overnight. To the reaction solution was added water, the mixture was extracted with diethyl ether, and the diethyl ether layer was washed with water and dried over magnesium sulfate. The diethyl ether was removed from the solution by evaporation, and the residue was purified by silica gel column chromatography using a mixture of hexane and diethyl ether as an eluent to give 2.27 g of isopropyl 3-benzoylacrylate as an oil.

$IR\nu_{max}^{neat}$, cm$^{-1}$: 1720 (ester), 1670 (ketone).

NMR(CDCl$_3$), ppm: 1.34 (6H, d, J=6 Hz), 5.17 (1H, heptet, J=6 Hz), 6.87 (1H, d, J=16 Hz), 7.46-7.70 (3H, m), 7.89 (1H, d, J=16 Hz), 8.01 (2H, d, J=8 Hz).

(2) Following the procedure of Example 19 using 2.18 g of isopropyl 3-benzoylacrylate in place of methyl 3-benzoylacrylate, there was obtained 2.85 g of isopropyl 2-acetylthio-3-benzoylpropionate as an oil.

$Ir\nu_{max}^{neat}$, cm$^{-1}$: 1730 (ester, thioester), 1685 (ketone),

NMR(CDCl$_3$), ppm: 1.23 (3H, d, J=6 Hz), 1.31 (3H, d, J=6 Hz), 2.38 (3H, s), 3.54 (1H, dd, J=18 Hz, 4 Hz), 3.72 (1H, dd, J=18 Hz, 7 Hz), 4.69 (1H, dd, J=7 Hz, 4 Hz), 5.06 (1H, heptet, J=6 Hz), 7.43-7.70 (3H, m), 7.98 (2H, d, J=8 Hz).

EXAMPLE 22

Following the procedure of Example 19 using 2.20 g of ethyl 3-(4-hydroxybenzoyl)acrylate in place of methyl 3-benzoylacrylate, there was obtained 2.78 g of ethyl 2-acetylthio-3-(4-hydroxybenzoyl)propionate as an oil.

$IR\nu_{max}^{neat}$, cm$^{-1}$: 1670 14 1730 (carbonyl).

NMR(CDCl$_3$), ppm: 1.26 (3H, t, J=8 Hz), 2.37 (3H, s), 3.52 (1H, dd, J=18 Hz, 5 Hz), 3.63 (1H, dd, J=18 Hz, 8 Hz), 4.21 (2H, q, J=8 Hz), 4.70 (1H, dd, J=8 Hz, 5 Hz), 6.84 (2H, d, J=8 Hz), 7.80 (2H, d, J=8 Hz).

EXAMPLE 23

(1) To a solution of 4.22 g of 3-(4-chlorobenzoyl)-acrylic acid in 40 ml of dimethylformamide were added 3.68 g of dimethyl sulfate and 1.36 g of potassium carbonate, and the mixture was stirred at room temperature for 3 hours. To the reaction solution was added diethyl ether. The mixture was washed, in turn, with water, a saturated aqueous solution of sodium hydrogencarbonate and water, and dried over magnesium sulfate. The diethyl ether was removed from the mixture by evaporation, and the residue was recrystallized from hexane to give 2.68 g of ethyl 3-(4-chlorobenzoyl)acrylate.
m.p. 62.5°-63.5° C.

(2) Following the procedure of Example 19 using 2.39 of ehtyl 3-(4-chlorobenzoyl)acrylate in place of methyl 3-benzoylacrylate, there was obtained 3.05 g of ethyl 2-acetylthio-3-(4-chlorobenzoyl)propionate as an oil.

$IR\nu_{max}^{neat}$, cm$^{-1}$: 1740 (ester, thioester), 1680 (ketone).

NMR(CDCl$_3$), ppm: 1.16 (3H, t, J=7 Hz), 2.38 (3H, s), 3.51 (1H, dd, J=16 Hz, 5 Hz), 3.69 (1H, dd, J=16 Hz, 7 Hz), 4.22 (2H, q, J=7 Hz), 4.71 (1H, dd, J=7 Hz, 5 Hz), 7.45 (2H, d, J=8 Hz), 7.91 (2H, d, J=8 Hz).

EXAMPLE 24

(1) Following the procedure of Example 23—(1) using 4.08 g of 3-(2,4-dimethylbenzoyl)acrylic acid in place of 3-(4-chlorobenzoyl)acrylic acid, there was obtained 4.00 g of ethyl 3-(2,4-dimethylbenzoyl)acrylate as an oil.

$Ir\nu_{max}^{neat}$, cm$^{-1}$: 1720 (ester), 1670 (ketone).

NMR(CDCl$_3$), ppm: 1.10 (3H, t, J=7 Hz), 2.36 (3H,s), 2.63 (3H, s), 4.05 (2H, q, J=7 Hz), 6.18 (1H, d, J=12 Hz), 6.89 (1H, d, J=12 Hz), 7.05 (1H, d, (2) Following the procedure of Example 19 using 2.32 g of ethyl 3-(2,4-dimethylbenzoyl)acrylate in place of methyl 3-benzoylacrylate, there was obtained 2.99 g of ethyl 2-acetylthio-3-(2,4-dimethylbenzoyl)propionate as an oil.

IR$\nu_{max}^{neat}$, cm$^{-1}$: 1740 (ester, thioester), 1680 (ketone).

NMR(CDCl$_3$), ppm: 1.27 (3H, t, J=7 Hz), 2.36 (3H, s), 2.38 (3H, s), 2.47 (1H, dd, J=18 Hz, 6 Hz), 2.50 (3H, s), 2.63 (1H, dd, J=18 Hz, 8 Hz), 4.22 (2H, q, J=7 Hz), 4.70 (1H, dd, J=8 Hz, 6 Hz), 7.07 (1H, s), 7.08 (1H, d, J=8 Hz), 7.64 (1H, d, J=8 Hz).

EXAMPLE 25

To a solution of 2.52 g of 2-acetylthio-3-benzoylpropionic acid in 20 ml of glacial acetic acid was added 4 ml of 10N sulfuric acid, and the mixture was refluxed at heating with stirring for 2 hours. The acetic acid was removed from the mixture by evaporation under reduced pressure, and ethyl acetate was added to the residue. The mixture was washed with water and dried over magnesium sulfate, and the ethyl acetate was removed from the mixture by evaporation. The residue was purified by silica gel column chromatograpy using a mixture of hexane and chloroform as an eluent, and then recrystallized from a mixture of hexane and diethyl ether to give 1.76 g of 3-benzoyl-2-mercaptopropionic acid.

m.p. 145°–146° C.

Elementary Anal. for C$_{10}$H$_{10}$O$_3$S. Calcd. (%): C 57.13, H 4.79. Found (%): C 57.28, H 4.87.

EXAMPLE 26

To a solution of 2.87 g of 2-acetylthio-3-(4-chlorobenzoyl)propionic acid in 50 ml of diethyl ether was added dropwise a solution of 0.95 g of 80% hydrazine hydrate in 5 ml of ethanol under ice-cooling with stirring over a period of 30 minutes. The mixture was stirred for a further 30 minutes. The reaction solution was washed with water and dried over magnesium sulfate. The diethyl ether was removed from the solution by evaporation, and the residue was purified by silica gel column chromatography using a mixture of hexane and diethyl ether as an eluent and recrystallized from the same mixture to give 1.01 g of 3-(4-chlorobenzoyl)-2-mercaptopropionic acid.

m.p. 134°–137° C.

Elementary Anal. for C$_{10}$H$_9$ClO$_3$S. Calcd. (%): C 49.09, H 3.71. Found (%): C 49.09, H 3.83.

EXAMPLE 27

To a solution of 2.80 g of ethyl 2-acetylthio-3-benzoylpropionate in 30 ml of ethanol was added 4 ml of 10N sulfuric acid, and the mixture was refluxed at heating with stirring for 4 hours. The ethanol was removed from the mixture by evaporation under redused pressure, and diethyl ether was added to the residue. The mixture was washed with water and dried over magnesium sulfate. The diethyl ether was removed from the mixture by evaporation, and the residue was purified by silica gel column chromatography using a mixture of hexane and diethyl ether as an eluent to give 1.62 g of ethyl 3-benzoyl-2-mercaptopropionate as an oil.

IR$\nu_{max}^{neat}$, cm$^{-1}$: 2540 (mercaptan), 1730 (ester), 1680 (ketone).

NMR(CDCl$_3$), ppm: 1.25 (3H, t, J=7 Hz), 2.27 (1H, d, J=8 Hz), 3.42 (1H, dd, J=17 Hz, 6 Hz), 3.73 (1H, dd, J=17 Hz, 8 Hz), 3.96 (1H, td, J=8 Hz, 5 Hz), 4.23 (2H, q, J=7 Hz), 7.42–7.70 (3H, m), 7.97 (2H, d, J=8 Hz).

EXAMPLE 28

Following the procedure of Example 27 using 3.15 g of ethyl 2-acetylthio-3-(4-chlorobenzoyl)propionate in place of ethyl 2-acetylthio-3-benzoylpropionate, there was obtained 1.88 g of ethyl 3-(4-chlorobenzoyl)-2-mercaptopropionate as an oil.

IR$\nu_{max}^{neat}$, cm$^{-1}$: 2560 (mercaptan), 1730 (ester), 1680 (ketone).

NMR(CDCl$_3$), ppm: 1.30 (3H, t, J=7 Hz), 2.26 (1H, d, J=7 Hz), 3.38 (1H, dd, J=17 Hz, 4 Hz), 3.70 (1H, dd, J=17 Hz, 7 Hz), 3.95 (1H, td, J=7 Hz, 4 Hz), 4.23 (2H, q, J=7 Hz), 7.49 (2H, d, J=8 Hz), 7.92 (2H, d, J=8 Hz).

EXAMPLE 29

To a solution of 2.10 g of 3-benzoyl-2-mercaptopropionic acid in 40 ml of dichloromethane were added 2.37 g of pyridine and 1.39 g of propionyl chloride under cooling at −20° C. with stirring, and the mixture was stirred at the same temperature for a further 30 minutes. To the reaction solution was added water, and the mixture was extracted with diethyl ether. The diethyl ether layer was washed, in turn, with water, dil. hydrochloric acid and water, and dried over magnesium sulfate. The diethyl ether was removed from the solution by evaporation, and the residue was purified by silica gel column chromatography using a mixture of hexane and diethyl ether as an eluent, and then recrystallized from a mixture of hexane and dichloromethane to give 2.16 g of 3-benzoyl-2-propionylthiopropionic acid.

m.p. 110°–112° C.

Elementary Anal. for C$_{13}$H$_{14}$O$_4$S. Calcd. (%): C 58.63, H 5.30. Found (%): C 58.43, H 5.20.

EXAMPLE 30

Following the procedure of Example 1 using 1.65 g of thiobenzoic acid in place of thioacetic acid, there was obtained 1.98 g of 3-benzoyl-2-benzoylthiopropionic acid.

m.p. 142.5°–144° C.

Elementary Anal. for C$_{17}$H$_{14}$O$_4$S. Calcd. (%): C 64.95, H 4.49. Found (%): C 65.17, H 4.57.

What is claimed is:

1. 3-benzoyl-2-mercaptopropionic acid derivatives represented by the formula:

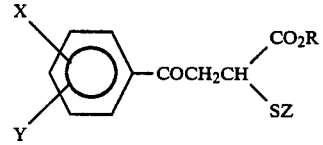

wherein
X represents a hydrogen atom, a halogen atom, hydroxy group, a lower alkyl group or a lower alkoxy group,
Y represents a hydrogen atom, a halogen atom, a lower alkyl group or a lower alkoxy group,
Z represents a hydrogen atom or a lower alkanoyl group, a benzoyl group or a toluoyl group, and
R represents a hydrogen atom or a lower alkyl group.

2. The 3-benzoyl-2-mercaptopropionic acid derivatives as claimed in claim 1, wherein the lower alkyl group is a methyl, ethyl, propyl, or isopropyl group.

3. The 3-benzoyl-2-mercaptopropionic acid derivatives as claimed in claim 1, wherein the lower alkoxy group is a methoxy or ethoxy group.

4. The 3-benzoyl-2-mercaptopropionic acid derivatives as claimed in claim 1, wherein the lower alkanoyl group is an acetyl, propionyl or butyryl group.

5. 2-Acetylthio-3-benzoylpropionic acid.
6. 2-Acetylthio-3-(4-methylbenzoyl)propionic acid.
7. 2-Acetylthio-3-(4-chlorobenzoyl)propionic acid.
8. 2-Acetylthio-3-(4-bromobenzoyl)propionic acid.
9. 3-benzoyl-2-mercaptopropionic acid.

* * * * *